US012597641B2

United States Patent

(12) United States Patent
Liu et al.

(10) Patent No.: US 12,597,641 B2
(45) Date of Patent: Apr. 7, 2026

(54) NON-AQUEOUS ELECTROLYTE, SECONDARY BATTERY, AND ELECTRICAL APPARATUS

(71) Applicant: Contemporary Amperex Technology (Hong Kong) Limited, Hong Kong (CN)

(72) Inventors: Jiao Liu, Ningde (CN); Limei Zhang, Ningde (CN); Peipei Chen, Ningde (CN); Jiamo Ren, Ningde (CN)

(73) Assignee: Contemporary Amperex Technology (Hong Kong) Limited, Hong Kong (CN)

( * ) Notice: Subject to any disclaimer, the term of this patent is extended or adjusted under 35 U.S.C. 154(b) by 0 days.

(21) Appl. No.: 19/211,299

(22) Filed: May 19, 2025

(65) Prior Publication Data

US 2025/0279477 A1 Sep. 4, 2025

Related U.S. Application Data

(63) Continuation of application No. PCT/CN2023/080454, filed on Mar. 9, 2023.

(51) Int. Cl.

| | |
|---|---|
| ***H01M 10/0567*** | (2010.01) |
| ***H01M 10/0525*** | (2010.01) |
| ***H01M 10/0568*** | (2010.01) |
| ***H01M 10/0569*** | (2010.01) |
| *C07D 327/10* | (2006.01) |

(52) U.S. Cl.

CPC ... *H01M 10/0567* (2013.01); *H01M 10/0525* (2013.01); *H01M 10/0568* (2013.01); *H01M 10/0569* (2013.01); *C07D 327/10* (2013.01); *H01M 2300/0025* (2013.01); *H01M 2300/0042* (2013.01)

(58) Field of Classification Search

CPC ......... H01M 10/0567; H01M 10/0569; H01M 10/0568; H01M 2300/0025; H01M 10/0525; H01M 2300/0042

See application file for complete search history.

(56) References Cited

U.S. PATENT DOCUMENTS

| | | | | |
|---|---|---|---|---|
| 2013/0171514 | A1 | 7/2013 | Mio et al. | |
| 2024/0213548 | A1* | 6/2024 | Shimizu ............ | H01M 10/0567 |

FOREIGN PATENT DOCUMENTS

| | | | |
|---|---|---|---|
| CN | 10547445 | A | 4/2016 |
| CN | 111755753 | A | 10/2020 |
| CN | 111934017 | A * | 11/2020 |
| CN | 112563573 | A | 3/2021 |
| CN | 114552004 | A | 5/2022 |
| CN | 114639872 | A | 6/2022 |
| CN | 115117446 | A | 9/2022 |
| CN | 115380416 | A * | 11/2022 |
| CN | 115692840 | A | 2/2023 |
| JP | 2017199548 | A | 11/2017 |
| JP | 2018156761 | A | 10/2018 |
| WO | 2021/093296 | A1 | 5/2021 |
| WO | 2022/143188 | A1 | 7/2022 |

OTHER PUBLICATIONS

International Search Report of PCT Application No. PCT/CN2023/080454, mailed Jun. 15, 2023, 4 pages with English translation.
Written Opinion of PCT Application No. PCT/CN2023/080454, mailed Jun. 15, 2023, 8 pages with English translation.
Notice of Allowance (with English Machine Translation), mailed Nov. 3, 2025, for corresponding Chinese Patent Application Serial No. 202380047772.8.
Office Action (with English Machine Translation), mailed Sep. 26, 2025, for corresponding Japanese Patent Application Serial No. 2025-524995.
Extended European Search Report, mailed Jan. 28, 2026, for corresponding European Patent Application Serial No. 23925769.4.

* cited by examiner

*Primary Examiner* — Laura Weiner
(74) *Attorney, Agent, or Firm* — K&L Gates LLP

(57) ABSTRACT

Provided are a non-aqueous electrolyte, a secondary battery, and an electrical apparatus. The non-aqueous electrolyte comprises an additive, the additive comprising a cyclic sulfate ester compound having the structure shown in general formula (I), wherein $R^1$, $R^2$, $R^3$, $R^4$, $R^5$, and $R^6$ are each independently selected from any one of: a group having the structure shown in general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, where n1, n2 and n3 are each independently any integer 0-2.

9 Claims, 2 Drawing Sheets

NON-AQUEOUS ELECTROLYTE, SECONDARY BATTERY, AND ELECTRICAL APPARATUS

CROSS-REFERENCE TO RELATED APPLICATIONS

This application is a continuation of PCT Application No. PCT/CN2023/080454, filed on Mar. 9, 2023, which is incorporated herein by reference in its entirety.

TECHNICAL FIELD

The present application relates to the technical field of batteries, and in particular, to a non-aqueous electrolytic solution, a secondary battery, and an electric device.

BACKGROUND

In recent years, with the development of lithium-ion secondary battery technology, lithium-ion secondary batteries have been widely used in energy storage power systems such as hydropower, thermal power, wind power, and solar power stations, as well as in various fields such as electric tools, electric bicycles, electric motorcycles, electric vehicles, military equipment, and aerospace. As lithium-ion secondary batteries have achieved great development, higher requirements have been placed on their fast-charging performance, cycle performance, safety performance, etc.

Among battery performances, long life is required, in particular, for lithium secondary batteries used in vehicles. Known causes of battery life deterioration include the continuous reduction of the electrolytic solution at the negative electrode during charging. To overcome these problems, attempts have been made to add various compounds to the electrolytic solution to form a passivation layer on the surface of the negative electrode, and this passivation layer is also known as the SEI film. This SEI film is a good conductor of lithium ions and a poor conductor of electrons, inhibiting the continuation of lithium-consuming reactions and serving to protect the electrode. Research indicates that forming a uniform, dense, stable, low-impedance, and well-adhered solid electrolyte interphase (SEI) film with excellent properties is beneficial for improving the electrochemical performance of batteries.

SUMMARY

The present application provides a non-aqueous electrolytic solution, a secondary battery, and an electric device to improve the cycle performance of the secondary battery.

A first aspect of the present application provides a non-aqueous electrolytic solution including an additive, and the additive includes a cyclic sulfate compound having a structure represented by general formula (I), general formula (I)

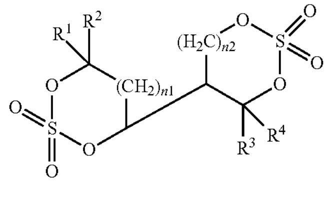

where $R^1$, $R^2$, $R^3$, and $R^4$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n1 and n2 are each independently any integer of 0-2;

general formula (II) is

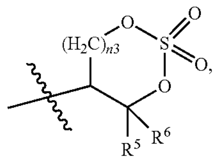

$R^5$ and $R^6$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n3 is any integer of 0-2;

$R^1$ and $R^2$ are not hydrogen atoms at the same time, and $R^3$ and $R^4$ are not hydrogen atoms at the same time;

or $R^1$, $R^2$, $R^3$, $R^4$, $R^5$, and $R^6$ satisfy the following conditions:

$R^1$ and $R^2$ are hydrogen atoms at the same time, one of $R^3$ and $R^4$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time;

or $R^1$, $R^2$, $R^3$, $R^4$, $R^5$, and $R^6$ satisfy the following conditions:

$R^3$ and $R^4$ are hydrogen atoms at the same time, one of $R^1$ and $R^2$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time.

The cyclic sulfate compound having general formula (I) described above, when used as an additive in a non-aqueous electrolytic solution, generates a more stable inorganic-organic mixed SEI film with a stronger electron-blocking ability on the negative electrode side during the first charging process of the secondary battery. The SEI film can block electrons and thus prevent the electrolytic solution from continuously decomposing at the negative electrode. Therefore, while the negative electrode plate has low resistance, the cycle performance of the battery cell is greatly improved, thereby significantly improving the battery life.

In any embodiment of the first aspect, the cyclic sulfate compound described above has a structure represented by general formula (I-1), general formula (I-1)

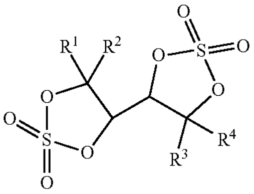

$R^1$, $R^2$, $R^3$, and $R^4$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group;

general formula (II-1) is

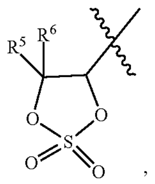, $R^5$ and $R^6$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group.

The cyclic sulfate rings in general formula (I-1) described above are all five-membered rings, which can form a denser SEI film. Compared with a six-membered ring, the five-membered ring has a greater ring tension and thus is easy to form a film at the positive and negative electrodes. The six-membered ring has a lower ring tension and higher stability, leading to slower film formation at the negative electrode, and consequently, the efficiency of generating an electron-blocking SEI film is lower, which affects the effect of the SEI film.

In any embodiment of the first aspect, optionally, $R^1$, $R^2$, $R^3$, $R^4$, $R^5$, and $R^6$ are each independently selected from any one of a group having a structure represented by general formula (II-1), a hydrogen atom, a halogen atom, a C1-C3 alkyl group, a C1-C3 haloalkyl group, a C1-C3 alkoxy group, a C1-C3 haloalkoxy group, a C2-C3 alkenyl group, a C1-C3 ester group, a cyano group, and a sulfonic acid group.

In any embodiment of the first aspect, optionally, $R^1$, $R^2$, $R^3$, $R^4$, $R^5$, and $R^6$ are each independently selected from any one of a group having a structure represented by general formula (II-1), a hydrogen atom, a halogen atom, a C1-C3 alkyl group, and a C1-C3 haloalkyl group.

In any embodiment of the first aspect, optionally, $R^1$, $R^2$, $R^3$, $R^4$, $R^5$, and $R^6$ are each independently selected from any one of a group having a structure represented by general formula (II-1), a hydrogen atom, an F atom, a C1 atom, a Br atom, a methyl group, an ethyl group, a propyl group, and an isopropyl group.

In any embodiment of the first aspect, optionally, the group having a structure represented by general formula (II-1) is selected from any one of the following groups:

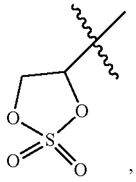, 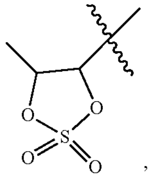, 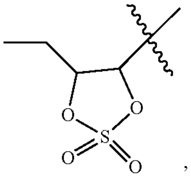, 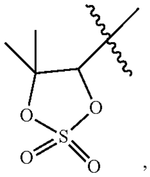, 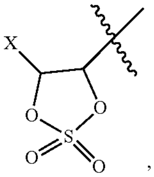, and 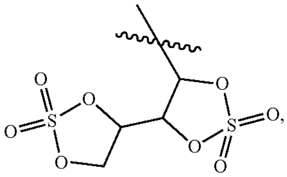

where X is an F atom, a Cl atom, or a Br atom.

In any embodiment of the first aspect, optionally, $R^1$, $R^2$, $R^3$, and $R^4$ are each independently selected from any one of

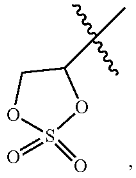, 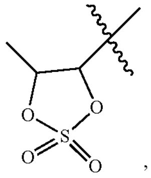, 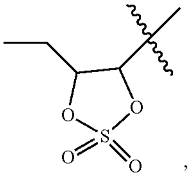, 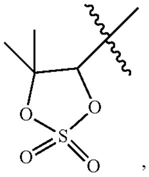, 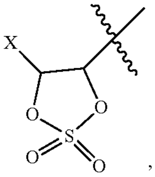, 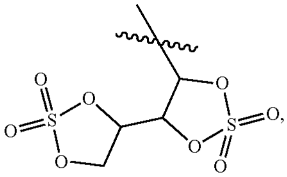

a hydrogen atom, an F atom, a Cl atom, a Br atom, a methyl group, an ethyl group, and a propyl group, and X is an F atom.

In any embodiment of the first aspect, optionally, $R^1$, $R^2$, $R^3$, and $R^4$ are each independently selected from any one of

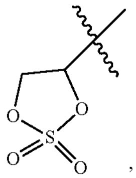, 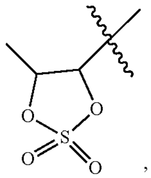, 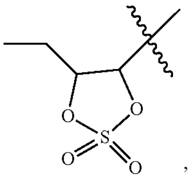,

-continued
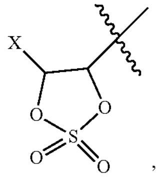
,
a hydrogen atom, a methyl group, and an ethyl group, and X is an F atom.
In any embodiment of the first aspect, the cyclic sulfate compound described above is selected from any one or more of the following compounds:
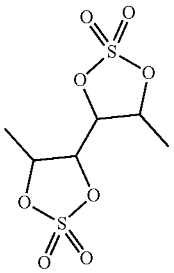
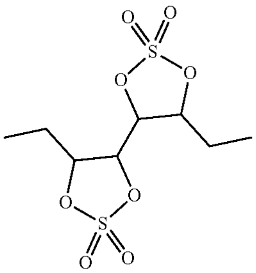
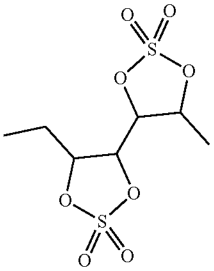
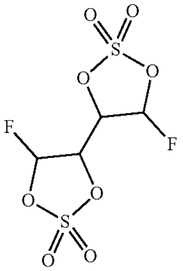
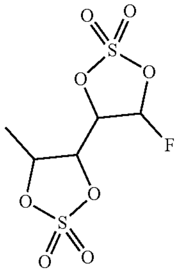
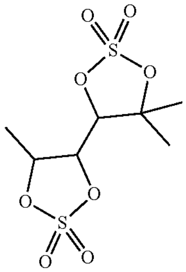
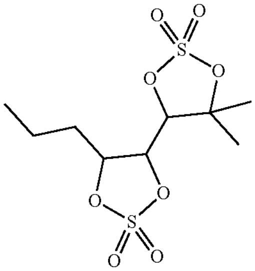
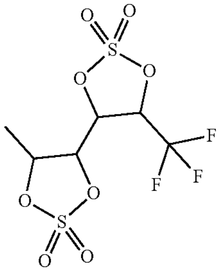
-continued
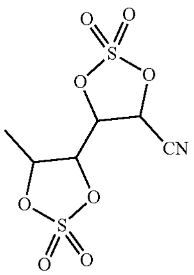
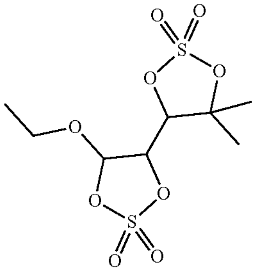
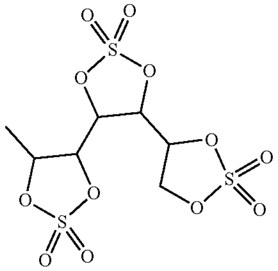
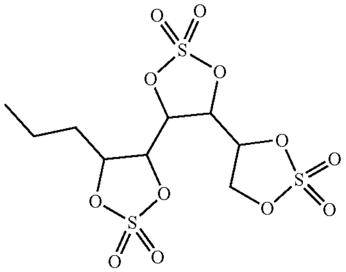
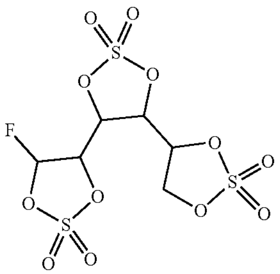
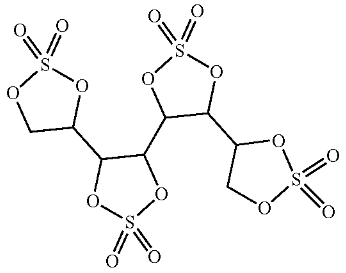
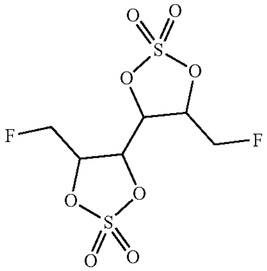
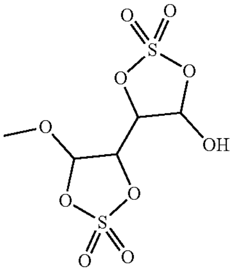

-continued

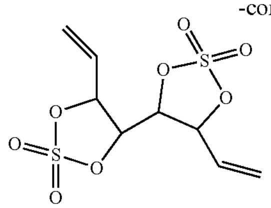
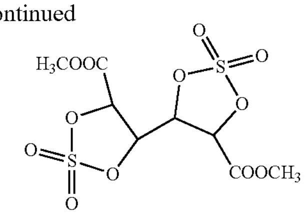
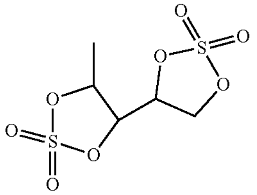
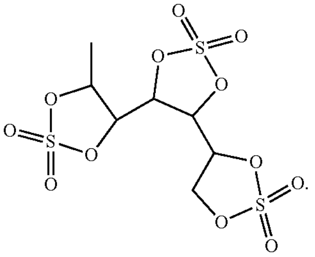

The preparation method for the cyclic sulfate compound described above is simpler and easier to promote and apply in industry, and it provides a more stable improvement in the cycle performance of secondary batteries.

In any embodiment of the first aspect, the mass content of the cyclic sulfate compound in the non-aqueous electrolytic solution described above is 0.001%-20%, for example, it may be 0.001%, 0.005%, 0.01%, 0.05%, 0.1%, 0.5%, 1%, 2%, 3%, 4%, 5%, 6%, 7%, 8%, 9%, 10%, 15%, or 20%, optionally 0.1%-10%, and further optionally 0.1%-5%, so as to utilize the cyclic sulfate compound to form a more stable organic-inorganic mixed SEI film with a stronger electron-blocking ability. This can not only effectively improve the cycle performance of the secondary battery, but also improve the output power of the secondary battery.

In any embodiment of the first aspect, the non-aqueous electrolytic solution described above further includes an electrolyte, and optionally, the electrolyte includes an alkali metal salt electrolyte; optionally, the electrolyte includes a lithium salt or a sodium salt; optionally, the lithium salt includes one or more selected from the group consisting of lithium hexafluorophosphate ($LiPF_6$), lithium perchlorate ($LiClO_4$), lithium hexafluoroarsenate ($LiAsF_6$), lithium bis(fluorosulfonyl)imide (LiFSI), and lithium bis(trifluoromethanesulfonyl)imide (LiTFSI), and the sodium salt includes one or more selected from the group consisting of sodium hexafluorophosphate, sodium difluoro(oxalato)borate, sodium perchlorate, sodium bis(fluorosulfonyl)imide, sodium bis(trifluoromethanesulfonyl)imide, and sodium trifluoromethanesulfonate. The lithium salts described above may be used alone or in a mixture of two or more than two.

In any embodiment of the first aspect, the non-aqueous electrolytic solution further includes a non-aqueous solvent, and the non-aqueous solvent includes any one or more of the group consisting of a cyclic carbonate, a chain carbonate, a nitrile solvent, a ketone solvent, and a sulfone solvent. Optionally, the non-aqueous solvent includes one or more of the group consisting of ethylene carbonate, propylene carbonate, ethyl methyl carbonate, diethyl carbonate, dimethyl carbonate, dipropyl carbonate, methyl propyl carbonate, ethyl propyl carbonate, butylene carbonate, fluoroethylene carbonate, methyl formate, methyl acetate, ethyl acetate, propyl acetate, methyl propionate, ethyl propionate, propyl propionate, methyl butyrate, ethyl butyrate, 1,4-butyrolactone, sulfolane, dimethyl sulfone, methyl ethyl sulfone, diethyl sulfone, tetrahydrofuran, dimethoxyethane, dioxolane, acetone, acetonitrile, and butyronitrile. The non-aqueous solvents described above may be used alone or in a mixture of two or more than two.

In any embodiment of the first aspect, the additive described above further includes one or more of sultone compounds to further improve the cycle performance of the battery. A second aspect of the present application provides a secondary battery including a positive electrode plate, an electrolytic solution, a separation film, and a negative electrode plate, and the electrolytic solution is any one of the non-aqueous electrolytic solutions described above. The output power and life of the secondary battery having the non-aqueous electrolytic solution of the present application are significantly improved.

A third aspect of the present application provides an electric device including a secondary battery, and the secondary battery includes any one of the secondary batteries described above. The service life of the electric device having the secondary battery of the present application is longer.

BRIEF DESCRIPTION OF THE DRAWINGS

To more clearly illustrate the technical solutions in the embodiments of the present application, the drawings required for illustrating the embodiments of the present application are briefly described below. Apparently, the drawings in the following description illustrate merely some embodiments of the present application, and those of ordinary skills in the art may still derive other drawings from these drawings without creative efforts.

Figure 1:
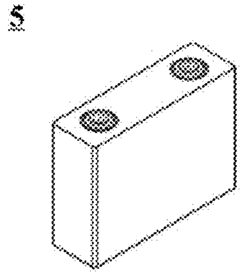
FIG. 1 is a schematic diagram of a secondary battery according to one embodiment of the present application.

The drawings are not drawn to scale.

DESCRIPTION OF THE REFERENCE NUMERALS

1: battery pack; 2: upper case body; 3: lower case body; 4: battery module; 5: secondary battery; 51: housing; 52: electrode assembly; 53: top cover assembly.

DETAILED DESCRIPTION

Implementations of the present application will be described in further detail with reference to the drawings and embodiments. The following detailed description of the embodiments and the drawings are used for the exemplary illustration of the principles of the present application, but are not intended to limit the scope of the present application. That is, the present application is not limited to the described embodiments.

Hereinafter, embodiments of the non-aqueous electrolytic solution, the secondary battery, and the electric device of the present application are specifically disclosed in detail with appropriate reference to the drawings. However, unnecessarily detailed descriptions may be omitted. For example, detailed descriptions of well-known matters and repetitive descriptions of actually identical structures may be omitted. This is to avoid unnecessary lengthiness of the following descriptions and to facilitate understanding by those skilled in the art. Additionally, the drawings and the following descriptions are provided to enable those skilled in the art to fully understand the present application and are not intended to limit the subject matter recited in the claims.

The "ranges" disclosed in the present application are defined with lower and upper limits. A given range is defined by selecting a lower limit and an upper limit that delineate the boundaries of a particular range. Ranges defined in this manner may include or exclude the end values and can be combined arbitrarily, which means that any lower limit may be combined with any upper limit to form a range. For example, if ranges of 60-120 and 80-110 are listed for a particular parameter, it is understood that ranges of 60-110 and 80-120 are also anticipated. Additionally, if the minimum range values listed are 1 and 2, and the maximum range values listed are 3, 4, and 5, then the following ranges can all be anticipated: 1-3, 1-4, 1-5, 2-3, 2-4, and 2-5. In the present application, unless otherwise specified, the numerical range "a-b" indicates an abbreviated representation of any combination of real numbers between a and b, where both a and b are real numbers. For example, the numerical range "0-5" indicates that all real numbers between "0-5" are listed herein, and "0-5" is merely an abbreviated representation of a combination of these numerical values. Additionally, when stating that a parameter is an integer ≥2, it is equivalent to disclosing that the parameter is, for example, an integer of 2, 3, 4, 5, 6, 7, 8, 9, 10, 11, 12, or the like.

Unless otherwise specified, all embodiments and optional embodiments of the present application can be combined with one another to form new technical solutions.

Unless otherwise specified, all technical features and optional technical features of the present application can be combined with one another to form new technical solutions.

Unless otherwise specified, all steps of the present application can be performed sequentially or randomly, preferably sequentially. For example, if the method includes steps (a) and (b), it indicates that the method may include steps (a) and (b) performed sequentially or steps (b) and (a) performed sequentially. For example, if the mentioned method may further include step (c), it indicates that step (c) may be added to the method in any order; for example, the method may include steps (a), (b), and (c), or steps (a), (c), and (b), or steps (c), (a), and (b), or the like.

Unless otherwise specified, the "include" and "comprise" mentioned in the present application are open-ended or closed-ended. For example, the "include" and "comprise" may mean that other unlisted components may also be included or comprised or that only the listed components are included or comprised.

Unless otherwise specified, the term "or" in the present application is inclusive. For example, the phrase "A or B" means "A, B, or both A and B". More specifically, any one of the following conditions satisfies the condition "A or B": A is true (or present) and B is false (or absent); A is false (or absent) and B is true (or present); or both A and B are true (or present).

[Secondary Battery]

Secondary batteries, also known as rechargeable batteries or storage batteries, refer to batteries that can continue to be used by reactivating their active materials through charging after discharging.

Typically, a secondary battery includes a positive electrode plate, a negative electrode plate, a separation film, and an electrolytic solution. During the charging and discharging process of the battery, active ions (such as lithium ions or sodium ions) are intercalated and deintercalated back and forth between the positive electrode plate and the negative electrode plate. The separation film is set between the positive electrode plate and the negative electrode plate to primarily prevent the positive and negative electrodes from short-circuiting, while allowing the passage of active ions. The electrolytic solution is between the positive electrode plate and the negative electrode plate, and primarily functions to conduct active ions.

[Non-Aqueous Electrolytic Solution]

One embodiment of the present application provides a non-aqueous electrolytic solution including an additive, and the additive includes a cyclic sulfate compound having a structure represented by general formula (I), general formula (I)

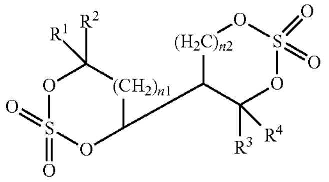

where $R^1$, $R^2$, $R^3$, and $R^4$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n1 and n2 are each independently any integer of 0-2;

general formula (II) is

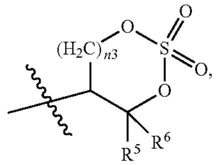

$R^5$ and $R^6$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n3 is any integer of 0-2;

$R^1$ and $R^2$ are not hydrogen atoms at the same time, and $R^3$ and $R^4$ are not hydrogen atoms at the same time;

or $R^1$, $R^2$, $R^3$, $R^4$, $R^5$, and $R^6$ satisfy the following conditions:

$R^1$ and $R^2$ are hydrogen atoms at the same time, one of $R^3$ and $R^4$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time;

or $R^1$, $R^2$, $R^3$, $R^4$, $R^5$, and $R^6$ satisfy the following conditions:

$R^3$ and $R^4$ are hydrogen atoms at the same time, one of $R^1$ and $R^2$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time.

The cyclic sulfate compound having general formula (I) described above, when used as an additive in a non-aqueous electrolytic solution, generates a more stable inorganic-organic mixed SEI film with a stronger electron-blocking ability on the negative electrode side during the first charging process of the secondary battery. The SEI film can block electrons and thus prevent the electrolytic solution from continuously decomposing at the negative electrode. While the negative electrode plate has low resistance, the cycle performance of the battery cell is greatly improved, thereby significantly improving the battery life.

The mechanism by which the cyclic sulfate compound described above achieves the effects described above is still unclear, but the applicant speculates that, based on the skeleton of the cyclic sulfate compound having two cyclic sulfate rings connected, by introducing substituents such as an alkyl group, an elastic SEI film with a longer organic chain can be generated at the negative electrode, and the SEI film can accommodate to the volume change of the negative electrode during cycling and prevent itself from destruction; by introducing substituents containing F, N, and the like, the substituents can participate in the film formation at the negative electrode to generate an SEI film rich in more inorganic components such as LiF and $Li_3N$, and in this way, the mechanical strength of the SEI film is improved, thereby improving the stability of the SEI film at the negative electrode and achieving the purpose of improving the cycle performance of the battery.

The alkyl group described above may be a linear alkyl group, a branched alkyl group, or a cycloalkyl group, including but not limited to, a methyl group, an ethyl group, a propyl group, an isopropyl group, an n-butyl group, an isobutyl group, a cyclopropanyl group, a cyclobutanyl group, etc.; the alkyl group in the haloalkyl group described above includes, but is not limited to, a linear alkyl group, a branched alkyl group, or a cycloalkyl group, such as a methyl group, an ethyl group, a propyl group, an isopropyl group, an n-butyl group, an isobutyl group, a cyclopropanyl group, and a cyclobutanyl group; the halogen atom may be a fluorine atom, a chlorine atom, or a bromine atom, and the halogen atom replaces any one or more hydrogen atoms on the alkyl group; the alkoxy group described above includes, but is not limited to, a cyclopropanyl group, an oxetanyl group, etc.; the halogen atom in the haloalkoxy group may be a fluorine atom, a chlorine atom, or a bromine atom, and the halogen atom replaces any one or more hydrogen atoms on the alkoxy group; the alkenyl group includes, but is not limited to, $—CH—CH_2$, $—CH{=}CH_2CH_3$, $—CH_2CH{=}CH_2$, and $—CH_2CH{=}CH_2CH_3$; the ester group includes, but is not limited to, a methyl formate group, an ethyl formate group, an ethyl acetate group, a methyl propionate group, an ethyl propionate group, a propyl propionate group, etc.

In some embodiments of the present application, the cyclic sulfate compound described above has a structure represented by general formula (I-1), general formula (I-1)

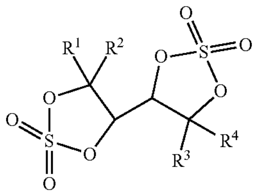

$R^1$, $R^2$, $R^3$, and $R^4$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group;

general formula (II-1) is

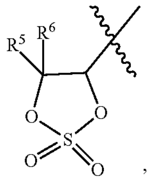

, $R^5$ and $R^6$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group.

The cyclic sulfate rings in general formula (I-1) described above are all five-membered rings, which can form a denser SEI film. Compared with a six-membered ring, the five-membered ring has a greater ring tension and thus is easy to form a film at the positive and negative electrodes. The six-membered ring has a lower ring tension and higher stability, leading to slower film formation at the negative electrode, and consequently, the efficiency of generating an electron-blocking SEI film is lower, which affects the effect of the SEI film.

In some embodiments of the present application, optionally, $R^1$, $R^2$, $R^3$, $R^4$, $R^5$, and $R^6$ are each independently selected from any one of a group having a structure represented by general formula (II-1), a hydrogen atom, a halogen atom, a C1-C3 alkyl group, a C1-C3 haloalkyl group, a C1-C3 alkoxy group, a C1-C3 haloalkoxy group, a C2-C3 alkenyl group, a C1-C3 ester group, a cyano group, and a sulfonic acid group.

In some embodiments of the present application, optionally, $R^1$, $R^2$, $R^3$, $R^4$, $R^5$, and $R^6$ are each independently selected from any one of a group having a structure represented by general formula (II-1), a hydrogen atom, a halogen atom, a C1-C3 alkyl group, and a C1-C3 haloalkyl group.

In some embodiments of the present application, optionally, $R^1$, $R^2$, $R^3$, $R^4$, $R^5$, and $R^6$ are each independently selected from any one of a group having a structure represented by general formula (II-1), a hydrogen atom, an F atom, a C1 atom, a Br atom, a methyl group, an ethyl group, a propyl group, and an isopropyl group.

In some embodiments of the present application, optionally, the group having a structure represented by general formula (II-1) is selected from any one of the following groups:

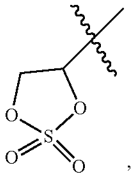 , 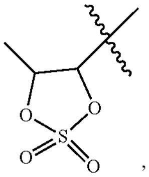 , 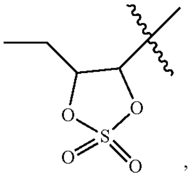 ,

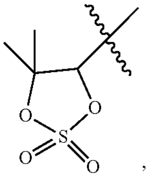 , 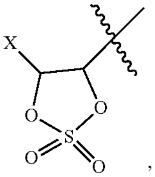 , and

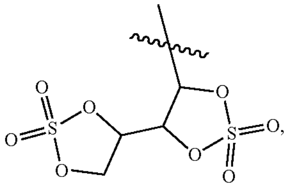

where X is an F atom, a C1 atom, or a Br atom.

In some embodiments of the present application, optionally, $R^1$, $R^2$, $R^3$, and $R^4$ are each independently selected from any one of

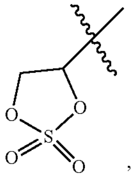 , 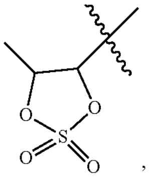 , 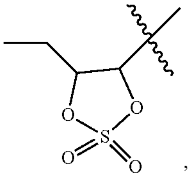 ,

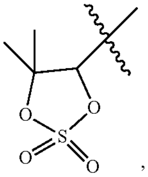 , 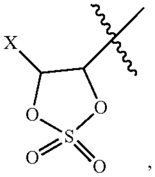 ,

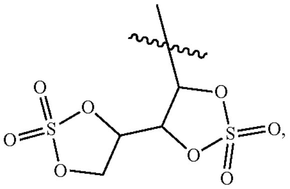

a hydrogen atom, an F atom, a Cl atom, a Br atom, a methyl group, an ethyl group, a propyl group, and an isopropyl group, and X is an F atom.

In some embodiments of the present application, optionally, $R^1$, $R^2$, $R^3$, and $R^4$ are each independently selected from any one of

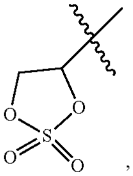 , 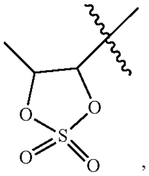 , 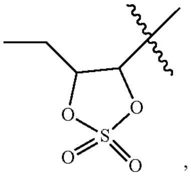 ,

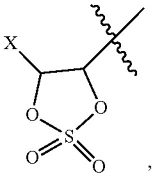 , a hydrogen atom, a methyl group, and an ethyl group, and X is an F atom.

In some embodiments of the present application, the cyclic sulfate compound described above is selected from any one or more of the following compounds:

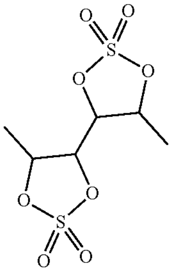 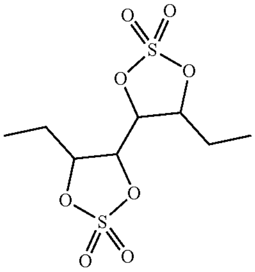

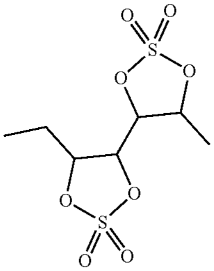 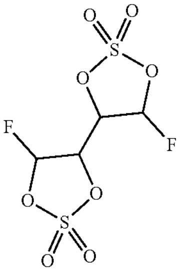

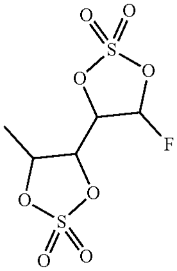 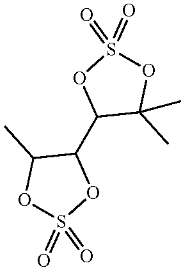

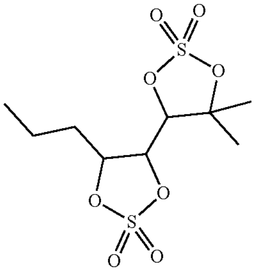 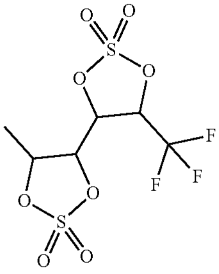

-continued

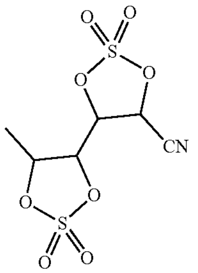

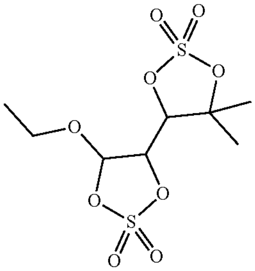

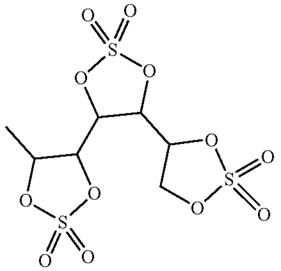

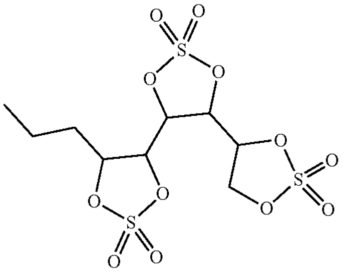

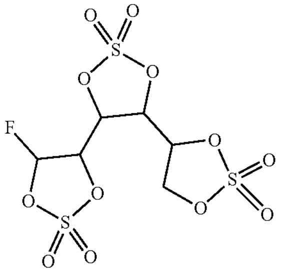

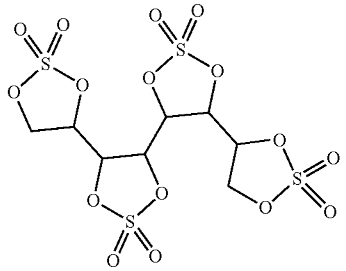

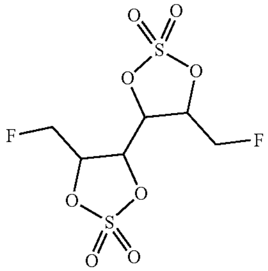

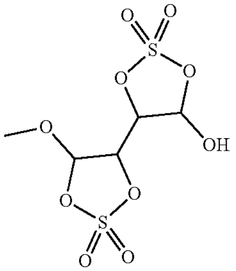

-continued

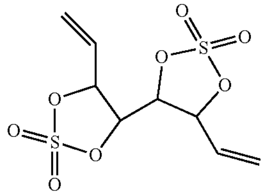

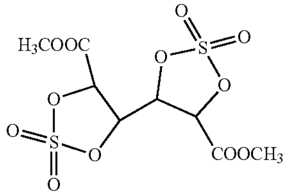

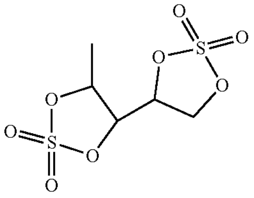

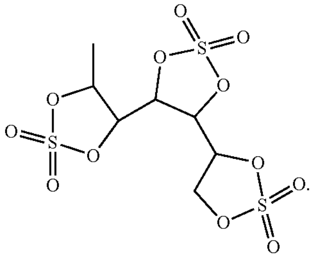

The preparation method for some of the cyclic sulfate compounds described above is simpler and easier to promote and apply in industry, and it provides a more stable improvement in the life of secondary batteries.

The amount of the cyclic sulfate compound in the embodiments described above of the present application can refer to the amount of a conventional cyclic sulfate compound in a conventional non-aqueous electrolytic solution. In some embodiments, the mass content of the cyclic sulfate compound in the non-aqueous electrolytic solution described above is 0.001%-20%, for example, it may be 0.001%, 0.005%, 0.01%, 0.05%, 0.1%, 0.5%, 1%, 2%, 3%, 4%, 5%, 6%, 7%, 8%, 9%, 10%, 15%, or 20%, optionally 0.1%-10%, and further optionally 0.1%-5%, so as to utilize the cyclic sulfate compound to form a more stable organic-inorganic mixed SEI film with a stronger electron-blocking ability. This can not only effectively improve the cycle performance of the secondary battery, but also improve the output power of the secondary battery. By limiting the mass content described above, it is possible to avoid the SEI film not fully functioning due to an insufficient content of the cyclic sulfate compound and to avoid the electrolytic solution becoming too viscous and a too-thick SEI film being formed at the negative electrode due to an excessive content of the cyclic sulfate compound, which would deteriorate the conductivity of the electrolytic solution and further deteriorate the improvement effect on cycle performance and charging capacity.

In some embodiments, the non-aqueous electrolytic solution further includes an electrolyte. Any electrolyte that can be commonly used in non-aqueous electrolytic solutions can be considered for use in the non-aqueous electrolytic solution of the present application. Those skilled in the art can select an electrolyte according to the battery system to which the non-aqueous electrolytic solution is applied, for example, select a conventional electrolyte suitable for lithium-ion secondary batteries or sodium-ion secondary batteries. In some embodiments, the electrolyte in the non-aqueous electrolytic solution described above includes an alkali metal salt electrolyte; optionally, the electrolyte includes a lithium salt or a sodium salt; optionally, the lithium salt includes one or more selected from the group consisting of lithium hexafluorophosphate ($LiPF_6$), lithium perchlorate ($LiClO_4$), lithium hexafluoroarsenate ($LiAsF_6$), lithium bis(fluorosulfonyl)imide (LiFSI), and lithium bis(trifluoromethanesulfonyl)imide (LiTFSI), and the sodium salt includes one or more selected from the group consisting of sodium hexafluorophosphate, sodium difluoro(oxalato) borate, sodium perchlorate, sodium bis(fluorosulfonyl)imide, sodium bis(trifluoromethanesulfonyl)imide, and sodium trifluoromethanesulfonate. The lithium salts or sodium salts described above may be used alone or in a mixture of two or more than two.

The content of the electrolyte in the non-aqueous electrolytic solution can refer to the electrolyte content in a conventional non-aqueous electrolytic solution. In some embodiments, the electrolyte content in the non-aqueous electrolytic solution is 0.1 mol/L-5 mol/L, for example, it may be 0.1 mol/L, 0.3 mol/L, 0.5 mol/L, 1 mol/L, 1.5 mol/L, 2 mol/L, 2.5 mol/L, 3 mol/L, 4 mol/L, or 5 mol/L, optionally 0.5 mol/L-1.5 mol/L, and further optionally 0.7 mol/L-1.2 mol/L.

The non-aqueous solvent of the present application can be selected from conventional non-aqueous solvents for secondary batteries. In some embodiments, the non-aqueous solvent includes any one or more of the group consisting of a cyclic carbonate, a chain carbonate, a nitrile solvent, a ketone solvent, and a sulfone solvent. Optionally, the non-aqueous solvent includes one or more selected from the group consisting of ethylene carbonate, propylene carbonate, ethyl methyl carbonate, diethyl carbonate, dimethyl carbonate, dipropyl carbonate, methyl propyl carbonate, ethyl propyl carbonate, butylene carbonate, fluoroethylene carbonate, methyl formate, methyl acetate, ethyl acetate, propyl acetate, methyl propionate, ethyl propionate, propyl propionate, methyl butyrate, ethyl butyrate, 1,4-butyrolactone, sulfolane, dimethyl sulfone, methyl ethyl sulfone, diethyl sulfone, tetrahydrofuran, dimethoxyethane, dioxolane, acetone, acetonitrile, and butyronitrile. The non-aqueous solvents described above may be used alone or in a mixture of two or more than two. For example, in order to improve the load characteristics and low-temperature characteristics of the secondary battery, a mixed solvent of a cyclic carbonate and a chain carbonate may be used. When the non-aqueous electrolytic solution of the present application is applied to a solid battery, a solid solvent such as dimethyl sulfone may be used.

In addition to the additives described above, the additive may further include a negative electrode film-forming additive or a positive electrode film-forming additive, or may include an additive capable of improving certain properties of the battery, such as an additive for improving the overcharge performance of the battery, an additive for improving the high- or low-temperature performance of the battery, or the like. In some embodiments, the additive described above further includes one or more of sultone compounds. By adding a sultone compound, the cycle performance of the secondary battery is further improved.

[Preparation Method for Cyclic Sulfate Compound Having Structure Represented by General Formula (I)]

The preparation method for the cyclic sulfate compound having a structure represented by general formula (I) of the present application refers to the following synthetic route:

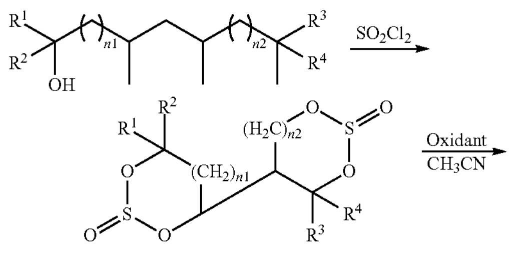

-continued

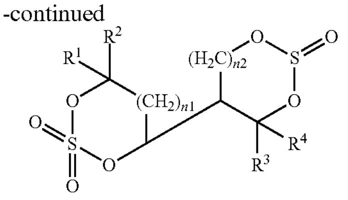

The reaction temperature of the first step is controlled at 30° C. to 60° C.; the reaction temperature of the second step is controlled at 10° C. to 30° C. In the second step, a catalyst such as ruthenium (III) chloride trihydrate is used for catalysis, and the oxidant may be sodium hypochlorite, ozone, or the like.

[Positive Electrode Plate]

A positive electrode plate generally includes a positive electrode current collector and a positive electrode film layer disposed on at least one surface of the positive electrode current collector, and the positive electrode film layer includes a positive electrode active material.

As an example, the positive electrode current collector has two surfaces opposite to each other in its own thickness direction, and the positive electrode film layer is disposed on any one or both of the two opposite surfaces of the positive electrode current collector.

In some embodiments, a metal foil or a composite current collector may be used as the positive electrode current collector. For example, as the metal foil, an aluminum foil may be used. The composite current collector may include a polymer material substrate and a metal layer formed on at least one surface of the polymer material substrate. The composite current collector can be formed by forming a metal material (aluminum, aluminum alloy, nickel, nickel alloy, titanium, titanium alloy, silver, silver alloy, etc.) on a polymer material substrate (such as polypropylene (PP), polyethylene terephthalate (PET), polybutylene terephthalate (PBT), polystyrene (PS), and polyethylene (PE)).

In some embodiments, a positive electrode active material for use in batteries known in the art may be used as the positive electrode active material. As an example, a positive electrode active material for a lithium-ion secondary battery may include at least one of the following materials: a lithium-containing phosphate with an olivine structure, a lithium transition metal oxide, and their respective modified compounds. However, the present application is not limited to these materials, and other traditional materials that can be used as positive electrode active materials for batteries may also be used. These positive electrode active materials may be used alone or in combination of two or more. Examples of the lithium transition metal oxide may include, but are not limited to, a lithium cobalt oxide (such as $LiCoO_2$), a lithium nickel oxide (such as $LiNiO_2$), a lithium manganese oxide (such as $LiMnO_2$ or $LiMn_2O_4$), a lithium nickel cobalt oxide, a lithium manganese cobalt oxide, a lithium nickel manganese oxide, and a lithium nickel cobalt manganese oxide (such as $LiNi_{1/3}Co_{1/3}Mn_{1/3}O_2$ (also referred to as $NCM_{333}$)). Examples of the lithium-containing phosphate with an olivine structure may include, but are not limited to, at least one of lithium iron phosphate (such as $LiFePO_4$ (also referred to as LFP)), a composite material of lithium iron phosphate and carbon, lithium manganese phosphate (such as $LiMnPO_4$), a composite material of lithium manganese phosphate and carbon, lithium manganese iron phosphate, and a composite material of lithium manganese iron phosphate and carbon.

As an example, a positive electrode active material for a sodium-ion secondary battery may include at least one of the following materials: a sodium transition metal oxide, a polyanionic compound, and a Prussian blue compound. However, the present application is not limited to these materials, and other traditional materials that can be used as positive electrode active materials for batteries may also be used. These positive electrode active materials may be used alone or in combination of two or more. In the sodium transition metal oxide, the transition metal includes at least one selected from the group consisting of Mn, Fe, Ni, Co, Cr, Cu, Ti, Zn, V, Zr, and Ce. The sodium transition metal oxide is, for example, $NaxMO_2$, where M includes one or more selected from the group consisting of Ti, V, Mn, Co, Ni, Fe, Cr, and Cu, and $0<x\leq 1$. The polyanionic compound may be a class of compounds having sodium ions, transition metal ions, and tetrahedral $(YO_4)^{n-}$ anion units, where the transition metal includes at least one selected from the group consisting of Mn, Fe, Ni, Co, Cr, Cu, Ti, Zn, V, Zr, and Ce; Y includes at least one selected from the group consisting of P, S, and Si; n represents the valence state of $(YO_4)^{n-}$. The polyanionic compound may also be a class of compounds having sodium ions, transition metal ions, tetrahedral $(YO_4)^{n-}$ anion units, and halogen anions, where the transition metal includes at least one selected from the group consisting of Mn, Fe, Ni, Co, Cr, Cu, Ti, Zn, V, Zr, and Ce; Y includes at least one selected from the group consisting of P, S, and Si, and n represents the valence state of $(YO_4)^{n-}$; the halogen includes at least one selected from the group consisting of F, C1, and Br. The polyanionic compound may also be a class of compounds having sodium ions, tetrahedral $(YO_4)^{n-}$ anion units, polyhedral units $(ZO_y)^{m+}$, and optional halogen anions, where Y includes at least one selected from the group consisting of P, S, and Si, and n represents the valence state of $(YO_4)^{n-}$; Z represents a transition metal, including at least one selected from the group consisting of Mn, Fe, Ni, Co, Cr, Cu, Ti, Zn, V, Zr, and Ce, and m represents the valence state of $(ZO_y)^{m+}$; the halogen includes at least one selected from the group consisting of F, Cl, and Br. The polyanionic compound includes at least one selected from the group consisting of $NaFePO_4$, $Na_3V_2(PO_4)_3$, $NaM'PO_4F$ (M' includes one or more selected from the group consisting of V, Fe, Mn, and Ni), and $Na_3(VO_y)_2(PO_4)_2F_{3-2y}$ $(0\leq y\leq 1)$. The Prussian blue compound may be a class of compounds having sodium ions, transition metal ions, and cyanide ions $(CN^-)$. The transition metal includes at least one selected from the group consisting of Mn, Fe, Ni, Co, Cr, Cu, Ti, Zn, V, Zr, and Ce. The Prussian blue compound is, for example, $Na_aMe_bMe'_c(CN)_6$, where Me and Me' each independently include at least one selected from the group consisting of Ni, Cu, Fe, Mn, Co, and Zn, and $0<a\leq 2$, $0<b<1$, and $0<c<1$.

In some embodiments, the positive electrode film layer further optionally includes a binder. As an example, the binder may include at least one of polyvinylidene fluoride (PVDF), polytetrafluoroethylene (PTFE), vinylidene fluoride-tetrafluoroethylene-propylene terpolymer, vinylidene fluoride-hexafluoropropylene-tetrafluoroethylene terpolymer, tetrafluoroethylene-hexafluoropropylene copolymer, and fluorinated acrylic resin.

In some embodiments, the positive electrode film layer further optionally includes a conductive agent. As an example, the conductive agent may include at least one of superconducting carbon, acetylene black, carbon black, Ketjen black, a carbon dot, a carbon nanotube, graphene, and a carbon nanofiber.

In some embodiments, the positive electrode plate can be prepared in the following manner: dispersing the components described above for preparing the positive electrode plate, such as the positive electrode active material, the conductive agent, the binder, and any other components, in a solvent (such as N-methylpyrrolidone) to form a positive electrode slurry; and coating the positive electrode current collector with the positive electrode slurry, and performing drying, cold pressing, and other processes, such that the positive electrode plate can be obtained.

[Negative Electrode Plate]

A negative electrode plate includes a negative electrode current collector and a negative electrode film layer disposed on at least one surface of the negative electrode current collector, and the negative electrode film layer includes a negative electrode active material.

As an example, the negative electrode current collector has two surfaces opposite to each other in its own thickness direction, and the negative electrode film layer is disposed on any one or both of the two opposite surfaces of the negative electrode current collector.

In some embodiments, a metal foil or a composite current collector may be used as the negative electrode current collector. For example, as the metal foil, a copper foil may be used. The composite current collector may include a polymer material substrate and a metal layer formed on at least one surface of the polymer material substrate. The composite current collector can be fabricated by forming a metal material (copper, copper alloy, nickel, nickel alloy, titanium, titanium alloy, silver, silver alloy, etc.) on a polymer material substrate (such as polypropylene (PP), polyethylene terephthalate (PET), polybutylene terephthalate (PBT), polystyrene (PS), and polyethylene (PE)).

In some embodiments, a negative electrode active material for use in batteries known in the art may be used as the negative electrode active material. As an example, the negative electrode active material may include at least one of the following materials: artificial graphite, natural graphite, soft carbon, hard carbon, a silicon-based material, a tin-based material, lithium titanate, and the like. The silicon-based material may be selected from at least one of elemental silicon, a silicon-oxygen compound, a silicon-carbon composite, a silicon-nitrogen composite, and a silicon alloy. The tin-based material may be selected from at least one of elemental tin, a tin-oxygen compound, and a tin alloy. However, the present application is not limited to these materials, and other traditional materials that can be used as negative electrode active materials for batteries may also be used. These negative electrode active materials may be used alone or in combination of two or more.

In some embodiments, the negative electrode film layer further optionally includes a binder. As an example, the binder may be selected from at least one of styrene-butadiene rubber (SBR), polyacrylic acid (PAA), sodium polyacrylate (PAAS), polyacrylamide (PAM), polyvinyl alcohol (PVA), sodium alginate (SA), polymethacrylic acid (PMAA), and carboxymethyl chitosan (CMCS).

In some embodiments, the negative electrode film layer further optionally includes a conductive agent. As an example, the conductive agent may be selected from at least one of superconducting carbon, acetylene black, carbon black, Ketjen black, a carbon dot, a carbon nanotube, graphene, and a carbon nanofiber.

In some embodiments, the negative electrode film layer further optionally includes other auxiliary agents, such as a thickener (e.g., sodium carboxymethylcellulose (CMC-Na)).

In some embodiments, the negative electrode plate can be prepared in the following manner: dispersing the components described above for preparing the negative electrode plate, such as the negative electrode active material, the conductive agent, the binder, and any other components, in a solvent (such as deionized water) to form a negative electrode slurry; and coating the negative electrode current collector with the negative electrode slurry, and performing drying, cold pressing, and other processes, such that the negative electrode plate can be obtained.

[Separation Film]

In some embodiments, the secondary battery further includes a separation film. The present application does not particularly limit the type of the separation film, and any porous-structure separation film known to have good chemical stability and mechanical stability may be selected and used.

In some embodiments, the separation film may be made of a material selected from at least one of glass fiber, non-woven fabric, polyethylene, polypropylene, and polyvinylidene difluoride. The separation film may be a single-layer film or a multi-layer composite film, and there is no particular limitation on this. When the separation film is a multi-layer composite film, the materials of the layers may be the same or different, and there is no particular limitation on this.

In some embodiments, the positive electrode plate, the negative electrode plate, and the separation film may be manufactured into an electrode assembly through a winding process or a stacking process.

In some embodiments, the secondary battery may include an outer packaging. The outer packaging can be used for packaging the electrode assembly and electrolyte described above.

In some embodiments, the outer packaging of the secondary battery may be a hard shell, such as a hard plastic shell, an aluminum shell, or a steel shell. The outer packaging of the secondary battery may also be a soft pack, such as a pouch-type soft pack. The soft pack may be made of plastic, and examples of the plastic may include polypropylene, polybutylene terephthalate, polybutylene succinate, and the like.

The present application does not particularly limit the shape of the secondary battery, and it may have a cylindrical shape, a prismatic shape, or any other shape. For example, FIG. 1 shows a secondary battery 5 having a prismatic structure as one example.

Figure 2:
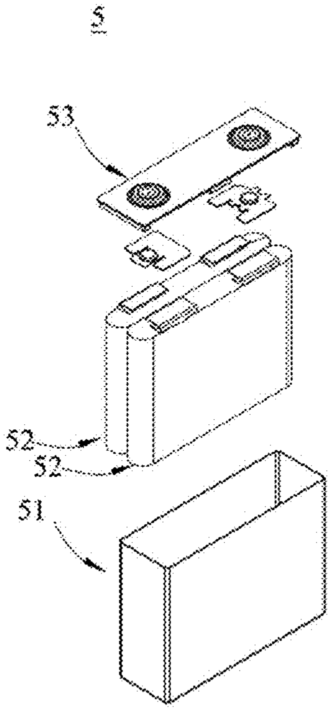
FIG. 2 is an exploded view of the secondary battery according to one embodiment of the present application as shown in FIG. 1.

In some embodiments, referring to FIG. 2, the outer packaging may include a housing 51 and a cover plate 53. The housing 51 may include a bottom plate and a side plate connected to the bottom plate, and the bottom plate and the side plate define, in an enclosing manner, an accommodating cavity. The housing 51 is provided with an opening communicating with the accommodating cavity, and the cover plate 53 is capable of lidding the opening to close the accommodating cavity. The positive electrode plate, the negative electrode plate, and the separation film may be subjected to a winding process or a stacking process to form an electrode assembly 52. The electrode assembly 52 is packaged in the accommodating cavity. The electrolytic solution is infiltrated into the electrode assembly 52. The number of the electrode assembly 52 included in the secondary battery 5 may be one or more, and those skilled in the art can select the number according to specific and actual needs.

In some embodiments, the secondary battery may be assembled into a battery module. The number of secondary batteries included in the battery module may be one or more, and the specific number may be selected by those skilled in the art based on the use and capacity of the battery module.

Figure 3:
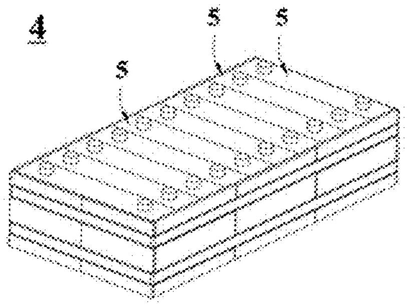
FIG. 3 is a schematic diagram of a battery module according to one embodiment of the present application.

FIG. 3 shows a battery module 4 as one example. Referring to FIG. 3, in the battery module 4, a plurality of secondary batteries 5 may be sequentially arranged in a length direction of the battery module 4. Certainly, the arrangement may also be in any other manner. Further, the plurality of secondary batteries 5 may be fixed by a fastener.

Optionally, the battery module 4 may further include a shell having an accommodating space in which the plurality of secondary batteries 5 are accommodated.

In some embodiments, the battery module described above may also be assembled into a battery pack. The number of battery modules included in the battery pack may be one or more, and the specific number may be selected by those skilled in the art based on the use and capacity of the battery pack.

Figure 4:
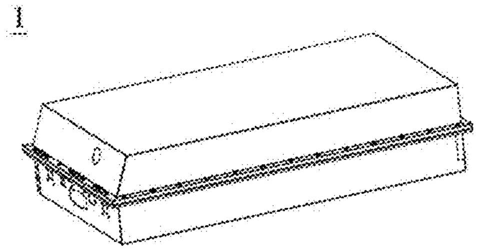
FIG. 4 is a schematic diagram of a battery pack according to one embodiment of the present application.
Figure 5:
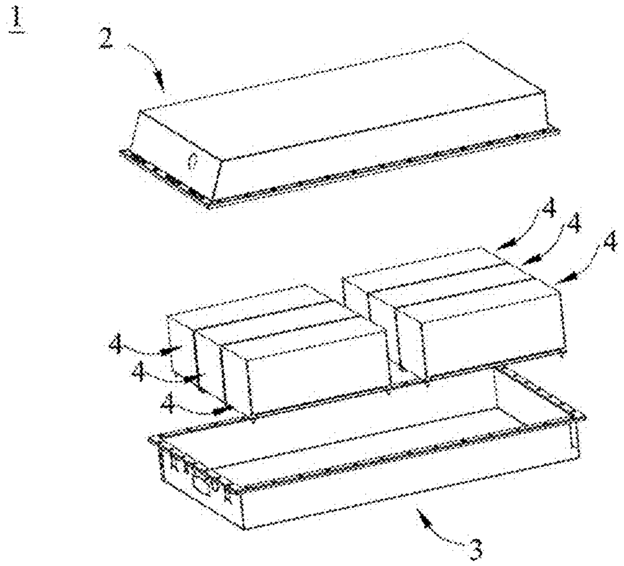
FIG. 5 is an exploded view of the battery pack according to one embodiment of the present application as shown in FIG. 4.

FIG. 4 and FIG. 5 show a battery pack 1 as one example. Referring to FIG. 4 and FIG. 5, the battery pack 1 may include a battery case and a plurality of battery modules 4 arranged in the battery case. The battery case includes an upper case body 2 and a lower case body 3. The upper case body 2 is capable of lidding the lower case body 3 to form a closed space for accommodating the battery modules 4. The plurality of battery modules 4 may be arranged in any manner in the battery case.

In addition, the present application further provides an electric device. The electric device includes at least one of the secondary battery, the battery module, or the battery pack provided in the present application. The secondary battery, the battery module, or the battery pack may be used as a power source for the electric device, and they may also be used as an energy storage unit for the electric device. The electric device may include, but is not limited to, a mobile device (e.g., a mobile phone or a laptop computer), an electric vehicle (e.g., a pure electric vehicle, a hybrid electric vehicle, a plug-in hybrid electric vehicle, an electric bicycle, an electric scooter, an electric golf cart, or an electric truck), an electric train, ship, or satellite, an energy storage system, or the like.

As the electric device, a secondary battery, a battery module, or a battery pack may be selected based on its use requirements.

Figure 6:
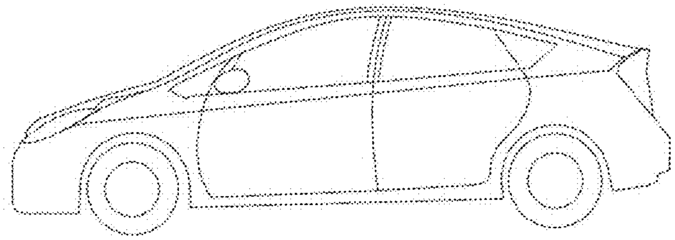
FIG. 6 is a schematic diagram of an electric device using a secondary battery as a power source according to one embodiment of the present application.

FIG. 6 shows an electric device as one example. The electric device is a pure electric vehicle, a hybrid electric vehicle, a plug-in hybrid electric vehicle, or the like. To meet the requirements of the electric device for high power and high energy density of the secondary battery, the battery pack or the battery module may be used.

EXAMPLES

Hereinafter, examples of the present application are described. The examples described below are illustrative and are merely used to explain the present application, and they should not be construed as limiting the present application. Examples without techniques or conditions specified therein are implemented according to techniques or conditions described in the literature in the art or according to product instructions. Reagents or instruments used herein without specified manufacturers are all commercially available conventional products. The information of other reagents or compounds is recorded in Table 1.

TABLE 1

| Substance | Structural formula | CAS No. |
|---|---|---|
| 1,6-Dideoxy-galactitol | 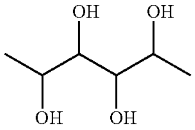 | 25289-20-7 |
| 3,4,5,6-Octanetetraol | 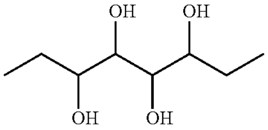 | 2165939-88-6 |
| 2,3,4,5-Heptanetetraol | 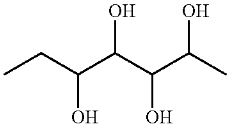 | 2629309-49-3 |
| 1,2,3,4,5,6-Heptanehexaol | 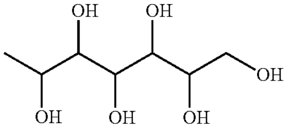 | 688007-16-1 |
| Octitol | 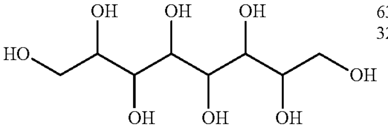 | 63976-32-9 |
| Compound 13 | 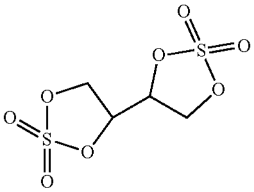 [SMILES: O=S1(=O)OCC(C2COS(=O)(=O)O2)O1] | 1431298-10-0 |
| Compound 14 | 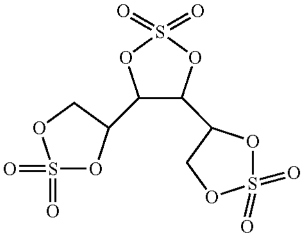 [SMILES: O=S1(=O)OCC(C2OS(=O)(=O)OC2C2COS(=O)(=O)O2)O1] | 2793408-99-6 |
| Compound 15 | 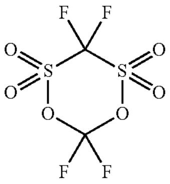 [SMILES: O=S1(=O)OC(F)(F)OS(=O)(=O)C1(F)F] | 446253-20-8 |
| Compound 16 | 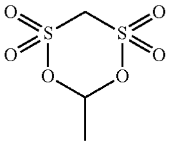 | 1860914-27-7 |

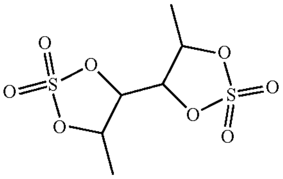 [SMILES: CC1OS(=O)(=O)OC1C1OS(=O)(=O)OC1C]

Synthesis Example 1: Synthesis of Compound 1

Step 1: 300 g (2 mol) of solid 1,6-dideoxygalactitol was added to a 2 L three-necked flask, and stirring was started. 523 g (4.4 mol) of thionyl chloride was added dropwise to the three-necked flask, with the temperature controlled around 15° C. during the process of dropwise addition. After the addition was completed, the mixture was reacted at 45° C. for 4 h with the temperature maintained. A large amount of paste-like solid was precipitated from the reaction solution. After cooling, 1 L of deionized water was slowly added dropwise, and the reaction system was quickly stirred to disperse. The obtained solid was filtered and subjected to slurrying and washing with deionized water multiple times until the pH was neutral. The filter cake was dried under reduced pressure at 60° C. to give an intermediate product.

Step 2: 184.2 g (0.8 mol) of intermediate product 1 was added to a 3 L three-necked flask, and 1000 mL of acetonitrile and 80 mg of ruthenium (III) chloride trihydrate catalyst were added. After being purged with nitrogen, the system was cooled to 20° C., and stirring was started. 2000 g of a 20% aqueous sodium hypochlorite solution was added dropwise within 1 h, and the reaction temperature was controlled at 10-20° C. After the addition was completed, the mixture was stirred at 10-20° C. for 10 min. The phases were separated, and the organic phase was quenched with an aqueous sodium sulfite solution until the potassium iodide-starch test paper did not turn blue. The phases were separated again, and the organic layer was concentrated. Acetonitrile was used for crystallization to give a white powder solid, which is compound 1 described above. 1H-NMR, $CD_3CN$, δ ppm 5.42-5.39 (m, 2H), 5.36-5.34 (m, 2H), 1.67-1.65 (d, 6H).

Synthesis Example 2: Synthesis of Compound 2

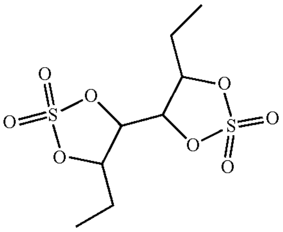 [SMILES: CCC1OS(=O)(=O)OC1C1OS(=O)(=O)OC1CC]

Step 1: 356.5 g (2 mol) of solid 3,4,5,6-octanetetraol was added to a 2 L three-necked flask, and stirring was started. 523 g (4.4 mol) of thionyl chloride was added dropwise to the three-necked flask, with the temperature controlled around 15° C. during the process of dropwise addition. After the addition was completed, the mixture was reacted at 45° C. for 4 h with the temperature maintained. A large amount of paste-like solid was precipitated from the reaction solution. After cooling, 1 L of deionized water was slowly added dropwise, and the reaction system was quickly stirred to disperse. The obtained solid was filtered and subjected to slurrying and washing with deionized water multiple times until the pH was neutral. The filter cake was dried under reduced pressure at 60° C. to give an intermediate product.

Step 2: 216.2 g (0.8 mol) of intermediate product 1 was added to a 3 L three-necked flask, and 1000 mL of acetonitrile and 80 mg of ruthenium (III) chloride trihydrate catalyst were added. After being purged with nitrogen, the system was cooled to 20° C., and stirring was started. 2000 g of a 20% aqueous sodium hypochlorite solution was added dropwise within 1 h, and the reaction temperature was controlled at 10-20° C. After the addition was completed, the mixture was stirred at 10-20° C. for 10 min. The phases were separated, and the organic phase was quenched with an aqueous sodium sulfite solution until the potassium iodide-starch test paper did not turn blue. The phases were separated again, and the organic layer was concentrated. Acetonitrile was used for crystallization to give compound 2.

Synthesis Example 3: Synthesis of Compound 3

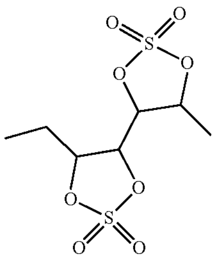 [SMILES: CCC1OS(=O)(=O)OC1C1OS(=O)(=O)OC1C]

Step 1: 328.4 g (2 mol) of solid 2,3,4,5-heptanetetraol was added to a 2 L three-necked flask, and stirring was started. 523 g (4.4 mol) of thionyl chloride was added dropwise to the three-necked flask, with the temperature controlled around 15° C. during the process of dropwise addition. After the addition was completed, the mixture was reacted at 45° C. for 4 h with the temperature maintained. A large amount of paste-like solid was precipitated from the reaction solution. After cooling, 1 L of deionized water was slowly added dropwise, and the reaction system was quickly stirred to disperse. The obtained solid was filtered and subjected to slurrying and washing with deionized water multiple times until the pH was neutral. The filter cake was dried under reduced pressure at 60° C. to give an intermediate product.

Step 2: 205 g (0.8 mol) of intermediate product 1 was added to a 3 L three-necked flask, and 1000 mL of acetonitrile was added. The mixture was stirred until the solid was completely dissolved, and 80 mg of ruthenium (III) chloride trihydrate catalyst was added. After being purged with nitrogen, the system was cooled to 20° C., and stirring was started. 2000 g of a 20% aqueous sodium hypochlorite solution was added dropwise within 1 h, and the reaction temperature was controlled at 10-20° C. After the addition was completed, the mixture was stirred at 10-20° C. for 10 min. The phases were separated, and the organic phase was quenched with an aqueous sodium sulfite solution until the potassium iodide-starch test paper did not turn blue. The phases were separated again, and the organic layer was concentrated. Acetonitrile was used for crystallization to give compound 3 (163.1 g, 82.8% yield).

Synthesis Example 4: Synthesis of Compound 4

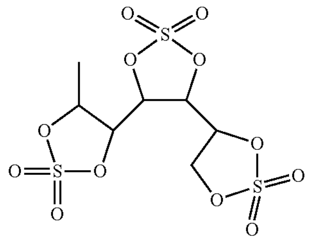 [SMILES: CC1OS(=O)(=O)OC1C1OS(=O)(=O)OC1C1COS(=O)(=O)O1]

Step 1: 392.4 g (2 mol) of solid 1,2,3,4,5,6-heptanehexaol was added to a 2 L three-necked flask, and stirring was started. 784.5 g (6.6 mol) of thionyl chloride was added dropwise to the three-necked flask, with the temperature controlled around 15° C. during the process of dropwise addition. After the addition was completed, the mixture was reacted at 45° C. for 4 h with the temperature maintained. A large amount of paste-like solid was precipitated from the reaction solution. After cooling, 1 L of deionized water was slowly added dropwise, and the reaction system was quickly stirred to disperse. The obtained solid was filtered and subjected to slurrying and washing with deionized water multiple times until the pH was neutral. The filter cake was dried under reduced pressure at 60° C. to give an intermediate product.

Step 2: 140 g (0.4 mol) of intermediate product 1 was added to a 4 L three-necked flask, and 1000 mL of acetonitrile and 110 mg of ruthenium (III) chloride trihydrate catalyst were added. After being purged with nitrogen, the system was cooled to 20° C., and stirring was started. 1500 g of a 20% aqueous sodium hypochlorite solution was added dropwise within 1 h, and the reaction temperature was controlled at 10-20° C. After the addition was completed, the mixture was stirred at 10-20° C. for 10 min. The phases were separated, and the organic phase was quenched with an aqueous sodium sulfite solution until the potassium iodide-starch test paper did not turn blue. The phases were separated again, and the organic layer was concentrated. Acetonitrile was used for crystallization to give compound 4.

Synthesis Example 5: Synthesis of Compound 5

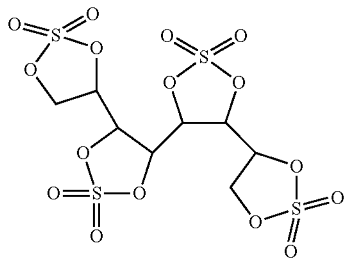 [SMILES: O=S1(=O)OCC(C2OS(=O)(=O)OC2C2OS(=O)(=O)OC2C2COS(=O)(=O)O2)O1]

Step 1: 484 g (2 mol) of solid octitol was added to a 2 L three-necked flask, and stirring was started. 1046 g (8.8 mol) of thionyl chloride was added dropwise to the three-necked flask, with the temperature controlled around 15° C. during the process of dropwise addition. After the addition was completed, the mixture was reacted at 45° C. for 4 h with the temperature maintained. A large amount of paste-like solid was precipitated from the reaction solution. After cooling, 1 L of deionized water was slowly added dropwise, and the reaction system was quickly stirred to disperse. The obtained solid was filtered and subjected to slurrying and washing with deionized water multiple times until the pH was neutral. The filter cake was dried under reduced pressure at 60° C. to give an intermediate product.

Step 2: 183.2 g (0.4 mol) of the intermediate product was added to a 4 L three-necked flask, and 1000 mL of acetonitrile and 150 mg of ruthenium (III) chloride trihydrate catalyst were added. After being purged with nitrogen, the system was cooled to 20° C., and stirring was started. 2000 g of a 20% aqueous sodium hypochlorite solution was added dropwise within 1 h, and the reaction temperature was controlled at 10-20° C. After the addition was completed, the mixture was stirred at 10-20° C. for 10 min. The phases were separated, and the organic phase was quenched with an aqueous sodium sulfite solution until the potassium iodide-starch test paper did not turn blue. The phases were separated again, and the organic layer was concentrated. Acetonitrile was used for crystallization to give compound 5.

In addition, the synthesis method for the compounds refers to Synthesis Example 1, using the corresponding substrates in Table 2 to replace 1,6-dideoxygalactitol.

| Compound | Chemical formula | Substrate | Compound LC-MS |
|---|---|---|---|
| 6 | 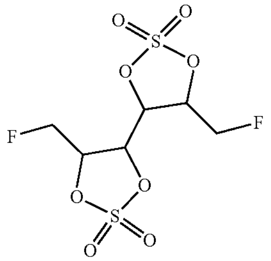 [SMILES: O=S1(=O)OC(CF)C(C2OS(=O)(=O)OC2CF)O1] | 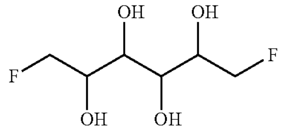 [SMILES: OC(CF)C(O)C(O)C(O)CF] CAS No.: 35827-51-1 | 310.25 |
| 7 | 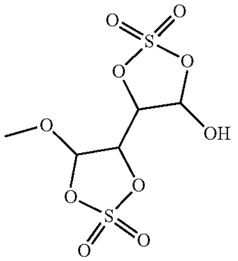 [SMILES: COC1OS(=O)(=O)OC1C1OS(=O)(=O)OC1O] | 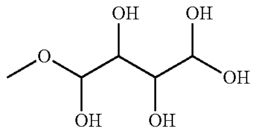 CAS No.: 113421-87-7 | 292.24 |
| 8 | 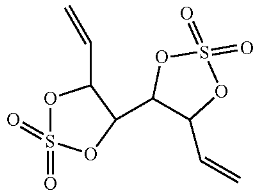 [SMILES: C=CC1OS(=O)(=O)OC1C1OS(=O)(=O)OC1C=C] | 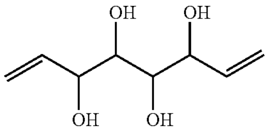 CAS No.: 301523-44-4 | 298.29 |
| 9 | 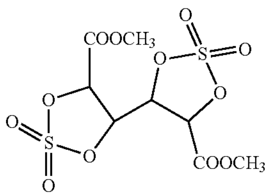 [SMILES: COC(=O)C1OS(=O)(=O)OC1C1OS(=O)(=O)OC1C(=O)OC] | 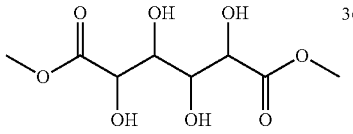 CAS No.: 24808-45-5 | 362.34 |
| 10 | 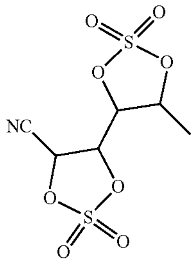 [SMILES: CC1OS(=O)(=O)OC1C1OS(=O)(=O)OC1C#N] | 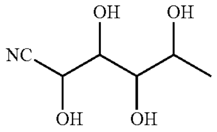 CAS No.: 7460-93-7 | 285.25 |

-continued

| Compound | Chemical formula | Substrate | Compound LC-MS |
|---|---|---|---|
| 11 | 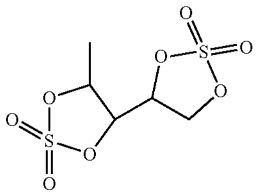 | 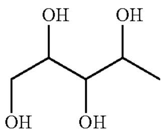 CAS No.: 25289-19-4 | 260.24 |
| 12 | 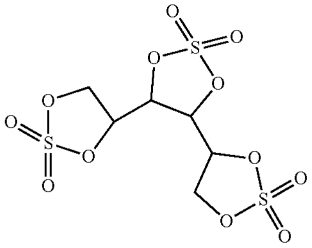 [SMILES: O=S1(=O)OCC(C2OS(=O)(=O)OC2C2COS(=O)(=O)O2)O1] | 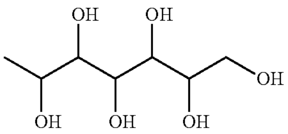 No.: 688007-16-1 | 382.33 |

Example 1

Electrolytic solution composition: Compound 1 was used as an additive, and its mass content in the electrolytic solution was 2%; lithium hexafluorophosphate $LiPF_6$ was used as an electrolyte, and its content in the electrolytic solution was 10%; a mixture of EC+EMC (ethylene carbonate+ethyl methyl carbonate) with a volume ratio of 3:7 was used as a solvent.

Preparation of Positive Electrode Plate:

The positive electrode active material lithium iron phosphate ($LiFePO_4$), the conductive agent acetylene black, and the binder polyvinylidene difluoride (PVDF) were dissolved in the solvent N-methylpyrrolidone (NMP) at a weight ratio of 90:5:5, and after the mixture was fully stirred and well mixed, a positive electrode slurry was obtained. The positive electrode current collector was evenly coated with the positive electrode slurry, followed by drying, cold pressing, and cutting to obtain a positive electrode plate.

Preparation of Negative Electrode Plate:

The negative electrode active material graphite, the conductive agent carbon black, the binder styrene-butadiene rubber (SBR), and the thickener sodium carboxymethylcellulose (CMC-Na) were dissolved in the solvent deionized water at a weight ratio of 90:4:4:2, and the mixture was well mixed to prepare a negative electrode slurry. The negative electrode current collector copper foil was evenly coated with the negative electrode slurry once or multiple times, followed by drying, cold pressing, and cutting to obtain a negative electrode plate.

Separation Film:

A conventional polypropylene film was used as the separation film.

Lithium-Ion Battery Assembly:

The positive electrode plate, the separation film, and the negative electrode plate were stacked in sequence, with the separation film placed between the positive and negative electrode plates to fulfill the function of separation. The stack was then wound to obtain an electrode assembly, and the electrode assembly was placed in a battery housing. After drying, the electrolytic solution was injected, and then a lithium-ion battery was obtained through processes such as formation and standing.

Example 2

Compound 2 was used to replace compound 1, and the rest was the same as in Example 1.

Example 3

Compound 3 was used to replace compound 1, and the rest was the same as in Example 1.

Example 4

Compound 4 was used to replace compound 1, and the rest was the same as in Example 1.

Example 5

Compound 5 was used to replace compound 1, and the rest was the same as in Example 1.

Example 6

Compound 6 was used to replace compound 1, and the rest was the same as in Example 1.

Example 7

Compound 7 was used to replace compound 1, and the rest was the same as in Example 1.

Example 8

Compound 8 was used to replace compound 1, and the rest was the same as in Example 1.

Example 9

Compound 9 was used to replace compound 1, and the rest was the same as in Example 1.

Example 10

Compound 10 was used to replace compound 1, and the rest was the same as in Example 1.

Example 11

Compound 11 was used to replace compound 1, and the rest was the same as in Example 1.

Example 12

Compound 12 was used to replace compound 1, and the rest was the same as in Example 1.

Example 13

The mass content of compound 1 was adjusted to 0.005%, and the rest was the same as in Example 1.

Example 14

The mass content of compound 1 was adjusted to 0.01%, and the rest was the same as in Example 1.

Example 15

The mass content of compound 1 was adjusted to 0.05%, and the rest was the same as in Example 1.

Example 16

The mass content of compound 1 was adjusted to 0.1%, and the rest was the same as in Example 1.

Example 17

The mass content of compound 1 was adjusted to 1%, and the rest was the same as in Example 1.

Example 18

The mass content of compound 1 was adjusted to 5%, and the rest was the same as in Example 1.

Example 19

The mass content of compound 1 was adjusted to 10%, and the rest was the same as in Example 1.

Example 20

The mass content of compound 1 was adjusted to 15%, and the rest was the same as in Example 1.

Example 21

The mass content of compound 1 was adjusted to 20%, and the rest was the same as in Example 1.

Example 22

The mass content of compound 1 was adjusted to 23%, and the rest was the same as in Example 1.

Example 23

1,3-Propane sultone (1,3-PS) was further added to the electrolytic solution as a second additive, and its mass content in the electrolytic solution was 1%. The rest was the same as in Example 1.

Example 24

Lithium bis(fluorosulfonyl)imide (LiFSI) was used to replace lithium hexafluorophosphate, and its mass content in the electrolytic solution was adjusted to 15.4%. The rest was the same as in Example 1.

Example 25

Lithium bis(trifluoromethanesulfonyl)imide (LiTFSI) was used to replace lithium hexafluorophosphate, and its mass content in the electrolytic solution was adjusted to 23.6%. The rest was the same as in Example 1.

Example 26

Electrolytic solution: Sodium hexafluorophosphate ($NaPF_6$) was used to replace lithium hexafluorophosphate, and its mass content in the electrolytic solution was adjusted to 13.8%. The rest was the same as in Example 1.

Preparation of positive electrode plate: The positive electrode active material $NaFePO_4$, the conductive agent acetylene black, and the binder polyvinylidene difluoride (PVDF) were fully stirred and well mixed in an N-methylpyrrolidone solvent system at a mass ratio of 80:10:10. An Al foil was then coated with the mixture, followed by drying and cold pressing to obtain a cathode plate.

Preparation of negative electrode plate: The negative electrode active material hard carbon, the conductive agent acetylene black, and the binder polyacrylic acid were fully stirred and well mixed in a deionized water solvent system at a mass ratio of 88:2:10. A copper foil was then coated with the mixture, followed by drying and cold pressing to obtain an anode plate.

The positive electrode plate, the negative electrode plate, and the polypropylene separation film were wound into a battery cell, which was then loaded into a battery packaging shell. The prepared electrolytic solution was injected, and then a sodium-ion battery was obtained through processes such as formation and standing.

Example 27

The composition of the solvent was adjusted to a mixed solution of EC+EMC with a volume ratio of 5:5, and the rest was the same as in Example 1.

Example 28

Diethyl carbonate (DEC) was used to replace EMC in the solvent, and the rest was the same as in Example 1.

Example 29

Ethyl propionate was used to replace EMC in the solvent, and the rest was the same as in Example 1.

Example 30

Tetrahydrofuran (THF) was used to replace EMC in the solvent, and the rest was the same as in Example 1.

Comparative Example 1

Compound 13 was used to replace compound 1, and the rest was the same as in Example 1.

Comparative Example 2

Compound 13 was used to replace compound 1, and its mass content in the electrolytic solution was adjusted to 0.5%. The rest was the same as in Example 1.

Comparative Example 3

Compound 13 was used to replace compound 1, and its mass content in the electrolytic solution was adjusted to 10%. The rest was the same as in Example 1.

Comparative Example 4

Compound 14 was used to replace compound 1, and the rest was the same as in Example 1.

Comparative Example 5

Compound 15 was used to replace compound 1, and the rest was the same as in Example 1.

Comparative Example 6

Compound 16 was used to replace compound 1, and the rest was the same as in Example 1.

Comparative Example 7

1,3-Propane sultone (1,3-PS) was used to replace compound 1, and the rest was the same as in Example 1.

Comparative Example 8

1,3-PS was used to replace compound 1, and the rest was the same as in Example 26.

Performance Testing:

1). Cycle Performance Testing

At 25° C., the lithium-ion battery was first fully discharged at 1 C and then tested. The testing procedure was as follows: The lithium-ion battery was charged at a constant current of 0.5 C until the voltage reached 3.65 V, followed by constant voltage charging at 3.65 V until the current dropped to 0.05 C. After 5 min of resting, the lithium-ion battery was discharged at a constant current of 0.5 C until the voltage dropped to 2.5 V. This is one charge-discharge cycle, and the discharge capacity of this cycle is considered the discharge capacity for the first cycle. The lithium-ion battery was subjected to multiple cycles of charge-discharge testing based on the method described above until the discharge capacity of the lithium-ion secondary battery decayed to 80%, and the number of cycles the lithium-ion battery underwent was recorded.

At 25° C., the sodium-ion battery was first fully discharged at 1 C and then tested. The testing procedure was as follows: The sodium-ion battery was charged at a constant current of 0.5 C until the voltage reached 3.95 V, followed by constant voltage charging at 3.95 V until the current dropped to 0.05 C. After 5 min of resting, the sodium-ion battery was discharged at a constant current of 0.5 C until the voltage dropped to 1.5 V. This is one charge-discharge cycle, and the discharge capacity of this cycle is considered the discharge capacity for the first cycle. The sodium-ion battery was subjected to multiple cycles of charge-discharge testing based on the method described above until the discharge capacity of the sodium-ion battery decayed to 80%, and the number of cycles the sodium-ion battery underwent was recorded.

Battery cycle capacity retention rate (%)=(discharge capacity of the battery in the Nth cycle/discharge capacity of the battery in the first cycle)×100%.

2). DCR Testing Under Normal Temperature

At room temperature, the lithium-ion battery was charged at a constant current of 1 C until the voltage reached 3.65 V, followed by constant voltage charging at 3.65 V until the current dropped to 0.05 C. After being fully charged, the battery was left to rest for 5 min, discharged at 1 C for 30 min (the battery cell had a charge of 50% SOC), and then left to rest for 5 min. The temperature was adjusted to 25° C. The battery cell was left to rest for 1 h, and the voltage V1 of the battery cell at this time was recorded. The battery cell was then discharged at 4 C for 30 s, and the voltage V2 after the pulse discharge was recorded. The DCR of the battery cell at 50% SOC when discharged for 30 s=(V1−V2)/I, where I=4 C.

At room temperature, the sodium-ion battery was charged at a constant current of 1 C until the voltage reached 4.2 V, followed by constant voltage charging at 4.2 V until the current dropped to 0.05 C. After being fully charged, the battery was left to rest for 5 min, discharged at 1 C for 30 min (the battery cell had a charge of 50% SOC), and then left to rest for 5 min. The temperature was adjusted to 25° C. The battery cell was left to rest for 1 h, and the voltage V1 of the battery cell at this time was recorded. The battery cell was then discharged at 4 C for 30 s, and the voltage V2 after the pulse discharge was recorded. The DCR of the battery cell at 50% SOC when discharged for 30 s=(V1−V2)/I, where I=4 C.

The test results are recorded in Table 3.

TABLE 3

| | 25° C. DCR (mohm) | Number of cycles to decay to 80% SOC at 25° C. |
|---|---|---|
| Example 1 | 12 | 2511 |
| Example 2 | 14 | 2498 |
| Example 3 | 13 | 2493 |
| Example 4 | 12 | 2509 |
| Example 5 | 15 | 2476 |
| Example 6 | 15 | 2021 |
| Example 7 | 17 | 1901 |
| Example 8 | 14 | 1955 |
| Example 9 | 15 | 1885 |
| Example 10 | 17 | 1832 |
| Example 11 | 16 | 1851 |
| Example 12 | 17 | 1811 |
| Example 13 | 20 | 2231 |
| Example 14 | 18 | 2302 |
| Example 15 | 16 | 2387 |
| Example 16 | 15 | 2401 |
| Example 17 | 14 | 2497 |
| Example 18 | 13 | 2508 |
| Example 19 | 14 | 2501 |
| Example 20 | 16 | 2408 |
| Example 21 | 18 | 2397 |
| Example 22 | 20 | 2302 |

TABLE 3-continued

| | 25° C. DCR (mohm) | Number of cycles to decay to 80% SOC at 25° C. |
|---|---|---|
| Example 23 | 15 | 2771 |
| Example 24 | 12 | 2401 |
| Example 25 | 12 | 2322 |
| Example 26 | 16 | 551 |
| Example 27 | 21 | 2301 |
| Example 28 | 19 | 2421 |
| Example 29 | 16 | 2121 |
| Example 30 | 19 | 2235 |
| Comparative Example 1 | 14 | 1651 |
| Comparative Example 2 | 17 | 1501 |
| Comparative Example 3 | 23 | 1387 |
| Comparative Example 4 | 27 | 2211 |
| Comparative Example 5 | 28 | 1821 |
| Comparative Example 6 | 30 | 1631 |
| Comparative Example 7 | 27 | 1642 |
| Comparative Example 8 | 25 | 351 |

It can be seen from the results of Examples 1 to 12 and Comparative Example 7 that the DCR and cycle performance of the battery cell can be effectively improved by introducing a cyclic sulfate additive, indicating that compared with a conventional sultone additive, the additive generates an SEI with lower interfacial impedance and higher stability at the negative electrode. Comparing Example 1 with Comparative Examples 1, 4, 5, and 6, the introduction of compound 1 can significantly improve the cycle performance of the battery cell. This is because, by introducing substituents such as an alkyl group, an elastic SEI with a longer organic chain can be generated at the negative electrode, and the SEI can accommodate to the volume change of the negative electrode during cycling and prevent itself from destruction, thereby improving the cycle performance of the battery cell.

It can be seen from the results of Examples 16 to 22 that an excessive amount of additive generates a thick SEI at the negative electrode, which deteriorates the conductivity of the electrolytic solution and results in increased polarization of the battery cell. To a certain extent, this deteriorates the cycle performance and DCR. When the mass proportion of the cyclic sulfonate additive of the present application in the electrolytic solution is within the preferred range described above, it can ensure that the battery cell has low DCR and good cycle performance.

Although the present application has been described with reference to preferred examples, various modifications can be made and components can be replaced with equivalents without departing from the scope of the present application. In particular, the technical features mentioned in the embodiments may be combined in any manner as long as there are no structural conflicts. The present application is not limited to the specific embodiments disclosed herein, but encompasses all technical solutions falling within the scope of the claims.

What is claimed is:

1. A non-aqueous electrolytic solution comprising a non-aqueous solvent, an electrolyte and an additive, wherein the non-aqueous solvent comprises a carbonate, the electrolyte comprises a lithium salt, the additive comprises a cyclic sulfate compound having a structure represented by formula (I), general formula (I)

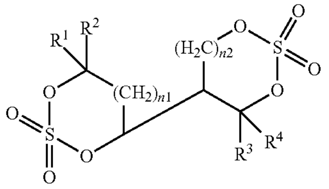

wherein $R^1$, $R^2$, $R^3$, and $R^4$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n1 and n2 are each independently any integer of 0-2;

formula (II) is

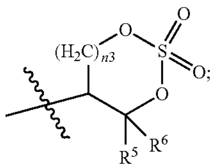

$R^5$ and $R^6$ are each independently selected from any one of a group having a structure represented by general formula (II), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and n3 is any integer of 0-2;

$R^1$ and $R^2$ are not hydrogen atoms at the same time, and $R^3$ and $R^4$ are not hydrogen atoms at the same time;

or $R^1$, $R^2$, $R^3$, $R^4$, $R^5$, and Re satisfy the following:

$R^1$ and $R^2$ are hydrogen atoms at the same time, one of $R^3$ and $R^4$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time;

or $R^1$, $R^2$, $R^3$, $R^4$, $R^5$, and $R^6$ satisfy the following:

$R^3$ and $R^4$ are hydrogen atoms at the same time, one of $R^1$ and $R^2$ is a hydrogen atom while the other is any one of a group having a structure represented by general formula (II), a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group, and $R^5$ and $R^6$ in the group having a structure represented by general formula (II) are not hydrogen atoms at the same time, a mass content of the cyclic sulfate compound in the non-aqueous electrolytic solution is 0.001%-20%.

2. The non-aqueous electrolytic solution according to claim 1, wherein the cyclic sulfate compound is selected from the group consisting of:
(I)a
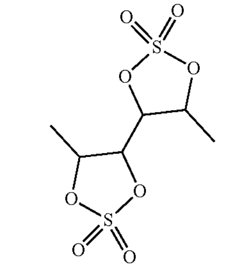
(I)b
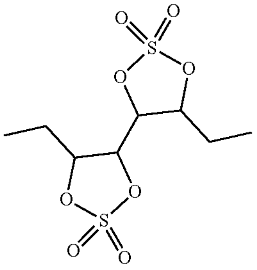
(I)c
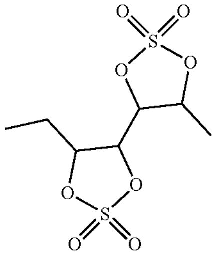
(I)d
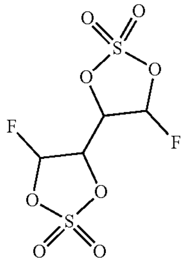
(I)e
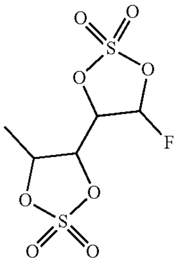
-continued
(I)f
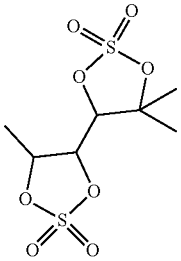
(I)g
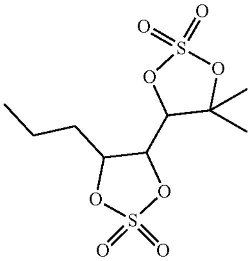
(I)h
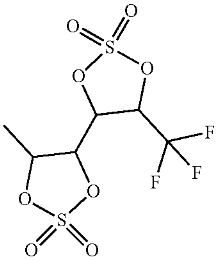
(I)i
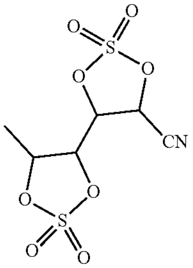
(I)j
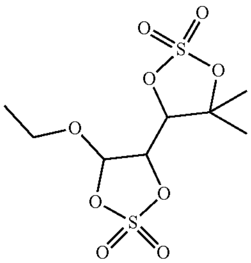
(I)k
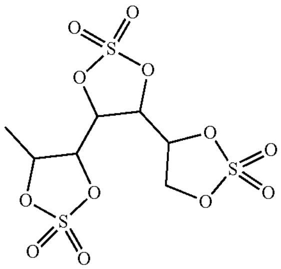

-continued (I)l

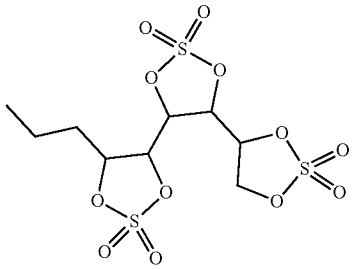

(I)m

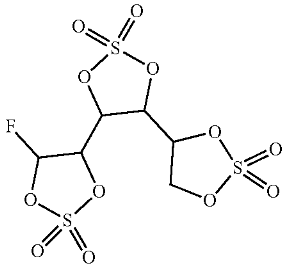

(I)n

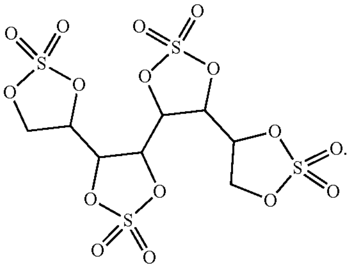

3. The non-aqueous electrolytic solution according to claim 1, wherein the cyclic sulfate compound has a structure represented by general formula (I-1), general formula (I-1)

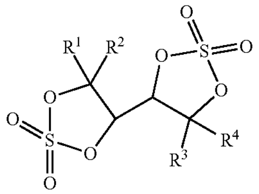

wherein $R^1$, $R^2$, $R^3$, and $R^4$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group;

general formula (II-1) is

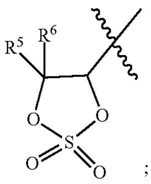

;

$R^5$ and $R^6$ are each independently selected from any one of a group having a structure represented by general formula (II-1), a hydrogen atom, a halogen atom, a C1-C6 alkyl group, a C1-C6 haloalkyl group, a C1-C6 alkoxy group, a C1-C6 haloalkoxy group, a C2-C6 alkenyl group, a C2-C6 ester group, a cyano group, and a sulfonic acid group.

4. The non-aqueous electrolytic solution according to claim 2, wherein $R^1$, $R^2$, $R^3$, $R^4$, $R^5$, and $R^6$ are each independently selected from any one of a group having a structure represented by general formula (II-1), a hydrogen atom, a halogen atom, a C1-C3 alkyl group, a C1-C3 haloalkyl group, a C1-C3 alkoxy group, a C1-C3 haloalkoxy group, a C2-C3 alkenyl group, a C1-C3 ester group, a cyano group, and a sulfonic acid group.

5. The non-aqueous electrolytic solution according to claim 1, wherein the carbonate of the non-aqueous solvent comprises one selected from the group consisting of a cyclic carbonate, a chain carbonate, and a mixture thereof, the cyclic carbonate is one selected from the group consisting of ethylene carbonate, propylene carbonate, butylene carbonate, fluoroethylene carbonate, and any combination thereof, and the chain carbonate is one selected from the group consisting of ethyl methyl carbonate, diethyl carbonate, dimethyl carbonate, dipropyl carbonate, methyl propyl carbonate, ethyl propyl carbonate, and any combination thereof.

6. The non-aqueous electrolytic solution according to claim 1, wherein the lithium salt is one selected from the group consisting of lithium hexafluorophosphate, lithium perchlorate, lithium hexafluoroarsenate, lithium bis(fluorosulfonyl)imide, lithium bis(trifluoromethanesulfonyl)imide, and any combination thereof.

7. The non-aqueous electrolytic solution according to claim 1, wherein the additive further comprises 1,3-propane sultone.

8. A secondary battery, comprising a positive electrode plate, an electrolytic solution, a separation film, and a negative electrode plate, wherein the electrolytic solution is the non-aqueous electrolytic solution according to claim 1.

9. An electric device, comprising a secondary battery, wherein the secondary battery comprises the secondary battery according to claim 8.

* * * * *